(12) United States Patent
Prass

(10) Patent No.: US 6,654,634 B1
(45) Date of Patent: Nov. 25, 2003

(54) METHOD AND APPARATUS FOR CONNECTION OF STIMULUS AND RECORDING ELECTRODES OF A MULTI-CHANNEL NERVE INTEGRITY MONITORING SYSTEM

(76) Inventor: Richard L. Prass, 1009 Caton Dr., Virginia Beach, VA (US) 23454

( * ) Notice: Subject to any disclaimer, the term of this patent is extended or adjusted under 35 U.S.C. 154(b) by 297 days.

(21) Appl. No.: 09/654,750

(22) Filed: Sep. 5, 2000

Related U.S. Application Data

(63) Continuation-in-part of application No. 09/212,380, filed on Dec. 16, 1998, now Pat. No. 6,181,961.
(60) Provisional application No. 60/069,877, filed on Dec. 16, 1997.

(51) Int. Cl.[7] ................................................. A61N 1/08
(52) U.S. Cl. ............................ 600/547; 600/522; 607/2
(58) Field of Search .............................. 607/2, 37, 115; 600/547, 548, 554, 522

(56) References Cited

U.S. PATENT DOCUMENTS

| | | | | |
|---|---|---|---|---|
| 3,936,126 A | * | 2/1976 | Miller | 439/441 |
| 4,351,343 A | * | 9/1982 | Parrillo et al. | 600/508 |
| 4,503,863 A | * | 3/1985 | Katims | 600/554 |
| 4,554,928 A | * | 11/1985 | Webster, Jr. | 600/522 |
| 5,343,869 A | | 9/1994 | Pross et al. | 600/301 |
| 5,509,822 A | * | 4/1996 | Negus et al. | 439/502 |
| 5,540,235 A | * | 7/1996 | Wilson | 600/554 |
| 5,557,210 A | * | 9/1996 | Cappa et al. | 324/539 |
| 5,666,958 A | * | 9/1997 | Rothenberg et al. | 600/509 |
| 5,782,892 A | * | 7/1998 | Castle et al. | 607/37 |
| 6,324,416 B1 | * | 11/2001 | Seibert | 600/386 |
| 6,349,228 B1 | * | 2/2002 | Kiani et al. | 600/323 |

* cited by examiner

*Primary Examiner*—Kennedy Schaetzle
(74) *Attorney, Agent, or Firm*—Ronald E. Prass, Jr.

(57) ABSTRACT

The invention provides a method and apparatus for connecting multiple electrodes into the receiving or head box portion of the nerve integrity monitor. The invention may provide patient connection electrodes, their transmission lines and a manner by which these components may communicate to the main monitoring unit to actuate automatic setup functions and instructions. The "off-line" setup and diagnostic instructions may be automatically initiated and annunciated to the main portion of the intraoperative nerve integrity monitor. The setup and diagnostic instructions may then automatically executed. The invention also may provide patient connection electrodes with improved resistance to the deleterious effects of spurious electromagnetic artifacts. The invention may also include the incorporation of both stimulation and recording electrodes with a single cable, but with the head boxes for recording and stimulation arranged in a staggered fashion along that cable. The recording electrode portion may appear at the terminal end of the cable and can be placed at the site of recording electrode placement. This arrangement allows use of shorter length electrodes, which may be cheaper to construct and less susceptible to electromagnetic and mechanical (drape movement) artifacts. The stimulus portion may be positioned more proximate to the main unit by several feet. After the recording portion is properly positioned, the stimulus connection box may be approximately at its optimal positioning for access after surgical draping. The all-in-one construction would obviate the need to separately place a stimulus head box apparatus, as for devices that include separate recording and stimulation head boxes and associated cabling. The invention may be particularly applicable for use in monitoring facial electromyograhic (EMG) activity during surgeries in which a facial motor nerve is at risk due to unintentional manipulation, as well as for other neural monitoring procedures.

16 Claims, 5 Drawing Sheets

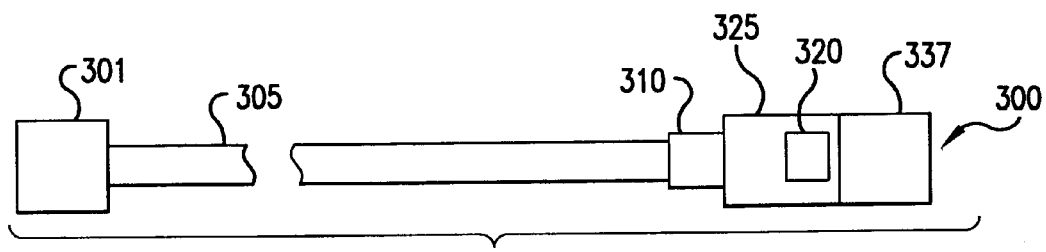
FIG. 3A
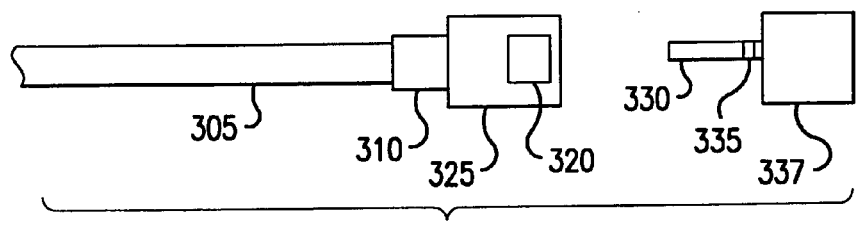
FIG. 3B
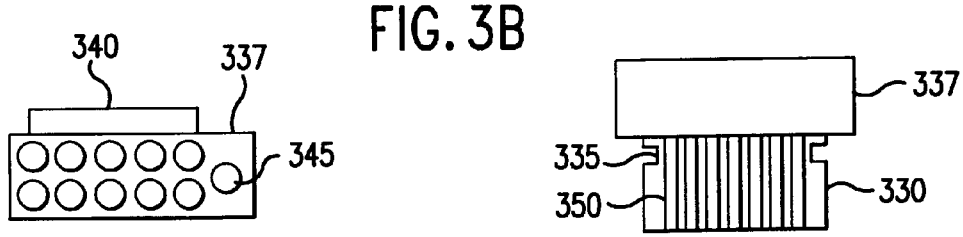
FIG. 3C FIG. 3D
FIG. 3E
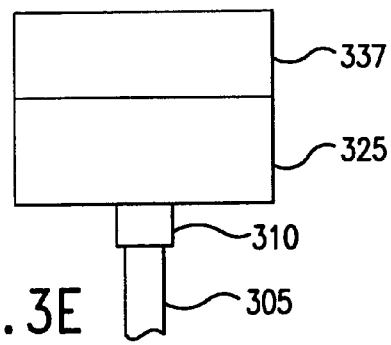
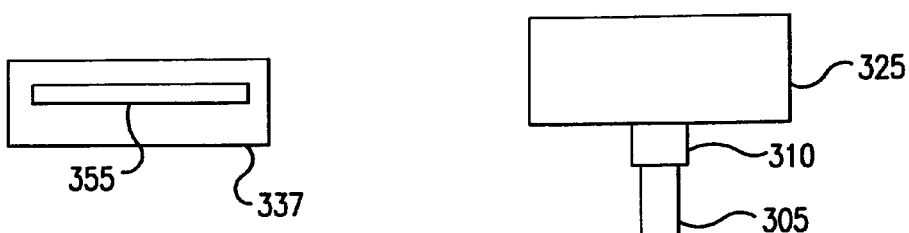
FIG. 3F FIG. 3G

METHOD AND APPARATUS FOR CONNECTION OF STIMULUS AND RECORDING ELECTRODES OF A MULTI-CHANNEL NERVE INTEGRITY MONITORING SYSTEM

This non-provisional application claims the benefit of U.S. Provisional Application No. 60/069,877, filed Dec. 16, 1997, and is a continuation-in-part of U.S. patent application Ser. No. 09/212,380, now U.S. Pat. No. 6,181,961, the subject matter of each being incorporated herein by reference.

BACKGROUND OF THE INVENTION

1. Field of the Invention

The invention relates to multi-channel nerve integrity monitoring, and more particularly to the patient connection electrodes, their transmission lines and a manner by which these components may be connected and communicate to the main monitoring unit to actuate automatic setup functions.

2. Description of Related Art

Despite advances in diagnostic, microsurgical and neurological techniques that enable a more positive anatomical identification of facial nerves, following surgical procedures to the head and neck, such as an acoustic neuroma resection, there is a significant risk of a patient losing facial nerve function. Because of the very delicate nature of these facial nerves, even the best and most experienced surgeons using the most sophisticated equipment known, encounter a considerable hazard that one or several nerves will be bruised, stretched or severed, during an operation.

However, studies have shown that preservation of facial nerves during an acoustic neuroma resection, for example, may be enhanced by the use of intraoperative electrical stimulation to assist in locating nerves. Broadly stated, the locating procedure, also known as nerve integrity monitoring, involves inserting sensing or recording electrodes directly within the cranial muscles innervated or controlled by the nerve of interest. Such an exemplary monitoring electrode is disclosed in U.S. Pat. No. 5,161,533 to Prass et al., which is incorporated herein by reference in its entirety.

One method of nerve localization involves the application of electrical stimulation near the area where the subject nerve is believed to be located. If the stimulation probe contacts or is located in the area reasonably close to the nerve, the stimulation signal applied to the nerve is transmitted through the nerve to excite the related muscle. Excitement of the muscle causes an electrical impulse to be generated within the muscle that is then transferred to the recording electrodes, thereby providing an indication to the surgeon as to the location of the nerve. Stimulation is accomplished using handheld monopolar or bipolar probes, such as the Electrical Stimulus Probe described in U.S. Pat. No. 4,892,105 to Prass, which is incorporated herein by reference in its entirety.

The Electrical Stimulus Probe (now known as the "Prass Flush-Tip Monopolar Probe") is insulated up to the distal tip to minimize current shunting through undesired paths. Another example of a bipolar probe is described in the U.S. Provisional Patent Application No. 60/096,243, entitled "Bipolar Electrical Stimulus Probe", filed Aug. 12, 1998, which is incorporated herein by reference in its entirety.

Another method of nerve localization involves the mechanical stimulation of the nerve of interest by various dissecting instruments. Direct physical manipulation of a motor nerve may cause the nerve to conduct a nerve impulse to its associated musculature. If those muscles are being monitored using a nerve integrity monitoring instrument, the surgeon will hear an acoustic representation of the muscle response in close temporal relationship to the antecedent mechanical stimulation. This will allow the nerve of interest to be roughly localized at the contact surface of the dissecting instrument.

Prior art nerve integrity monitoring instruments (such as the Xomed® NIM-2® XL Nerve Integrity Monitor) have proven to be effective for performing the basic functions associated with nerve integrity monitoring, such as recording Electromyogram (EMG) activity from muscles innervated by an affected nerve and alerting a surgeon when the affected nerve is activated by application of a stimulus signal. However, these nerve integrity monitoring instruments have significant limitations for some surgical applications and in some operating room environments, as discussed below.

For example, a significant limitation in the majority of prior art nerve integrity monitoring devices is the availability of only two channels for monitoring of EMG activity. This two channels monitoring capability provides a limited ability to monitor multiple nerves or multiple branches of single nerves. In addition, a limited number of channels does not allow for redundancy in the event of electrode failure.

In some cases, such as with monitoring the facial nerve during the performance of parotidectomy, monitoring must be performed from each of four major branches of the facial nerve. Alternatively, procedures involving the more proximal (closer to the brainstem origin) portion of the facial nerve may be effectively monitored by a single channel, in that the nerve exhibits no topographical organization in that location. With only two channels available, there is also limited ability to distinguish whether recorded signal events represent artifacts or EMG responses, based upon their distribution among "intelligent" and "non-intelligent" electrodes, as described in U.S. patent application Ser. No. 09/213,015, filed on Dec. 16, 1998. That is, true or important EMG signals provoked by surgical manipulations distribute "intelligently" only to muscles supplied by the nerve of interest. In contrast, electrical artifacts distribute "non-intelligently" to all proximate electrodes within an electrical or electromagnetic field. Thus a multi-channel recording capability allows the user to distinguish artifacts and EMG signal events on the basis of such distribution.

Another advantage of multi-channel recording is that, with the availability of some redundancy, different recording strategies may be used for recording signals from the muscles supplied by a single nerve of interest, in order to take advantage of their respective advantages and minimize their inherent disadvantages. The most commonly used recording method for intraoperative nerve integrity monitoring involves intramuscular placement of two closely spaced electrodes. The use of intramuscular electrodes in close bipolar arrangement (as described in U.S. Pat. No. 5,161,533) is preferred in order to obtain adequate spatial selectivity and maintenance of high common mode rejection characteristics in the signal conditioning pathway for reduced interference by electromagnetic artifacts. Such electrode configurations yield a compressed dynamic range of electrical voltage observed between the paired electrodes. For example, if it is physically situated near one of the electrodes, a single motor unit (activation of a single nerve fiber) may cause an adequate voltage deflection to be heard as a clear signal spike or to exceed a predetermined voltage threshold. Moreover, with close electrode spacing and bipolar amplification, recording of larger responses is frequently associated with internal signal cancellation, which significantly reduces the amplitude of the observed electrical signal. The resultant compressed dynamic range is advantageous for supplying direct or raw EMG signal feedback to the operating surgeon, in that both large and small signal events may be clearly and comfortably heard at one volume setting. However, the method offers a limited ability to fractionate responses based upon their overall magnitude.

For quantitative measurements of EMG response amplitudes, a preferential recording method involves the use of surface electrodes in a monopolar arrangement, with an active electrode placed over a suitable muscle, supplied by the nerve of interest, and the other electrode placed at a relative distance away in an electrically neutral site. The active electrode summates muscle activity over a greater or more representative area than intramuscular electrodes and the absence of a simultaneous signal in the inactive ("indifferent reference") electrode eliminates unpredictable signal cancellation seen in bipolar recording where both electrodes in a pair detect the same signal from different perspectives. Measurement of the response amplitude using this recording method provides an excellent representative measure of relative magnitude of muscle activation. However, the monopolar ("indifferent reference") arrangement with surface electrodes provides a poor quality signal for acoustic (loudspeaker) feedback to the operating surgeon. With multi-channel recording capability, this method of EMG recording may be employed in parallel with closely spaced intramuscular electrodes in order to achieve better signal quality With the stated potential advantages afforded by multi-channel recording capability, some devices are known to include up to eight channels of EMG recording capability. However, while multi-channel recording affords the possible advantages stated above, it poses a significant disadvantage of requiring greater complexity of off-line diagnostic or system check, and recording setup procedures. This is especially true if certain channels are designated for quantitative purposes using a monopolar method and others are used for feedback to the operating surgeon with closely spaced intramuscular electrodes. Thus, a method is needed that would allow a surgeon to take advantage of the flexibility afforded by a multi-channel EMG recording capability, while reducing the relative complexty of setup and diagnostic functions.

Another problem posed by the availability of a greater number of EMG recording channels, in the setting of coventional art, is that all electrodes are provided individually or in kits with separate connectors for each lead. Furthermore, "protected" pin connectors required by conventional devices are more bulky and cumbersome to use than the "standard" pin connectors. Regardless of color coding and other labeling strategies, with multiple recording electrodes, placing the connector pins in the electrode receiving portion ("head box") of the nerve integrity monitor can be quite tedious, time consuming, and confusing, such this configuration may result inaccuracy regarding proper placement of the connectors.

Another problem related to multiple channel recording is that the head box portion of the nerve integrity monitoring, which receives the electrodes placed in various locations on the patient, must be of a sufficient size to accommodate all of the necessary connections. The larger size of the head box may render it more susceptible to electromagnetic noise and may be too large to allow it to be placed physically near the area where the electrodes are placed. Multiple channel head boxes are typically placed under the operating table, because they cannot be placed close to the electrode sites.

Accordingly, the remote location of the head box results in electrode leads being typically one meter in length or longer. Electrode leads are typically unshielded from the effects of electromagnetic noise, and the longer the length of the leads, the more susceptible they are to such interference. One method of improving the resistance of electrode leads to electromagnetic noise is to arrange them in a "twisted-pair" fashion, as described in U.S. Pat. No. 5,161,533. Such an arrangement better preserves common mode rejection capabilities within the signal path than otherwise untreated leads. Therefore, a method that allows reduction of the size of the head box apparatus or otherwise further reduces the potential electromagnetic interference in the electrode leads would be desired.

SUMMARY OF THE INVENTION

The invention provides a method and apparatus for connecting multiple electrodes into the receiving or head box portion of the nerve integrity monitor. The invention may provide patient connection electrodes, their transmission lines and a manner by which these components may communicate to the main monitoring unit to actuate automatic setup functions and instructions. The "off-line" setup and diagnostic instructions may be automatically initiated and annunciated to the main portion of the intraoperative nerve integrity monitor. The setup and diagnostic instructions may then automatically executed. The invention also may provide patient connection electrodes with improved resistance to the deleterious effects of spurious electromagnetic artifacts.

The invention may also include the incorporation of both stimulation and recording electrodes with a single cable, but with the head boxes for recording and stimulation arranged in a staggered fashion along that cable. The recording electrode portion may appear at the terminal end of the cable and can be placed at the site of recording electrode placement. This arrangement allows use of shorter length electrodes, which may be cheaper to construct and less susceptible to electromagnetic and mechanical (drape movement) artifacts. The stimulus portion may be positioned more proximate to the main unit by several feet. After the recording portion is properly positioned, the stimulus connection box may be approximately at its optimal positioning for access after surgical draping. The all-in-one construction would obviate the need to separately place a stimulus head box apparatus, as for devices that include separate recording and stimulation head boxes and associated cabling.

The invention is particularly applicable for use in monitoring facial electromyograhic (EMG) activity during surgeries in which a facial motor nerve is at risk due to unintentional manipulation, although it will be appreciated that the invention has broader applications and can be used in other neural monitoring procedures.

BRIEF DESCRIPTION OF THE DRAWINGS

The invention is described in detailed with reference to the following drawings, wherein like numerals represent like elements, and wherein:

FIGS. 3A–3G are diagrams of an exemplary patient connection recording harness;

DETAILED DESCRIPTION OF PREFERRED EMBODIMENTS

The invention embodies a method and apparatus by which the patient connection procedure and other aspects of "off-line" setup prior to multi-channel nerve integrity monitoring is made simpler, less cumbersome, and less time-consuming. The patient connection procedure and "off-line" setup is based upon the construction of special multi-electrode patient-connection ("kits"), a patient connection harness and the manner by which certain aspects of the patient-connection kits communicate specific information to the main portion of the nerve integrity monitor regarding setup parameters. The construction of the patient connection kits and harness also reduces the likelihood of electromagnetic interference than with standard electrode connections. In the discussion below, there is a relatively strong conceptual separation between off-line control (performed at some time other than during the surgical procedure) and on-line control (performed during a surgical procedure), as pertains to control of intraoperative neurophysiological monitoring system functions through the use of input devices. For purposes of the discussion below, "off-line" operations are performed when monitoring is not actively being performed, for example, as when logging-in patient information, setting system preferences or retrieving saved-data for "post-production" analysis, whereas "on-line" refers to periods of active intraoperative neurophysiological monitoring, which involves the monitoring functions of nerve localization and function assessment. The use of the present invention pertains to, but is not limited to, "off-line" control of functions of the intraoperative nerve integrity monitor.

Figure 1:
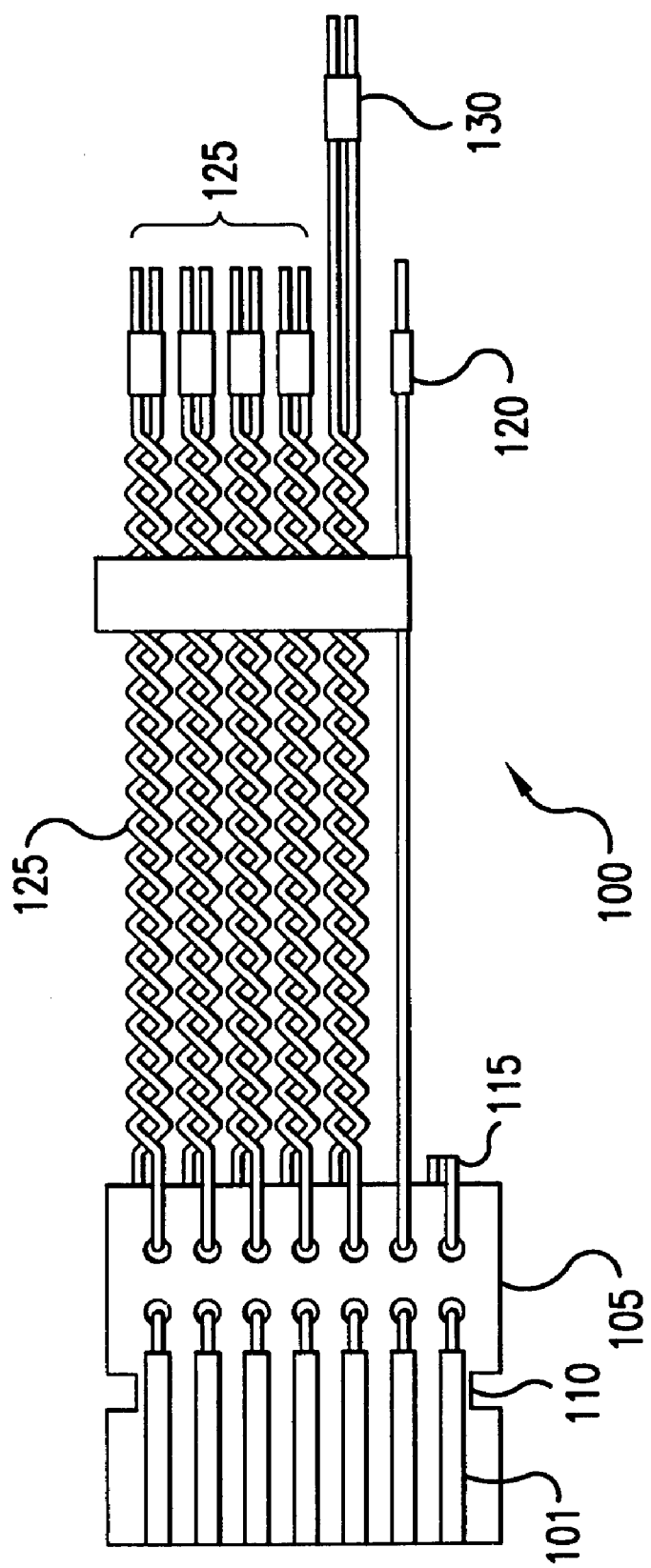
FIG. 1 is a diagram of an exemplary multi-electrode patient connection apparatus.

FIG. 1 is an exemplary diagram of a multi-electrode patient-connection apparatus (or "kit") 100 with four paired bipolar "intelligent" data electrodes and one artifact-detection electrode ("4+1"). All electrodes terminate in conductor strips or electrical contacts 101 on a connector 105 constructed (a male connector is shown as an exemplary connector in this embodiment) from double-sided PC board stock, for example. The connector 105 contains a notch 110 or other irregular feature that may be used to firmly hold the connector in the proper position by a spring-loaded latch. One pair of contacts 101 on the connector 105 is shorted by a jumper 115, or any other electrical connection providing an equivalent function. One unpaired connection is made with a single patient ground electrode 120. In the present embodiment, there are four paired bipolar electrodes 125 and one artifact-detection electrode 130. When the connector 105 is connected to the main monitoring unit, electrical contact with the circuitry in the main monitoring unit by the electrical contacts 101, signals the initiation of the automatic setup.

As described above, for the purposes of the description of FIG. 1 above and FIG. 2 below, multiple recording electrodes 125,130, soldered or otherwise pre-connected to a multi-pin (contact) connector, will be termed a kit 100. Each kit 100 consists of the above-described multiple EMG recording electrodes 125, a single artifact-detection electrode 130, a single patient ground electrode 120 and a single multi-contact connector with compact dimensions.

The length of the EMG electrode leads 125 is 18 inches, which is approximately one-half of the length of conventional electrodes. Thus, the EMG electrodes 125 of the invention are less susceptible to electromagnetic noise. The single 1 cm (subdermal) ground electrode 120 is also 18 inches in length or somewhat greater. The artifact-detection electrode 130 is 24 inches greater in length in order that the leads may be looped over the area where the other EMG electrodes 125 are inserted, thus, creating a mild antenna effect for detecting electromagnetic artifacts.

Within the connector 105 of the patient-connection kits 100 are multiple additional pairs of contacts 101, across which there may be no (or an open) connection. A short or jumper wire 115, or a fixed resistor of varying absolute value may be connected across the additional contact pairs 101 so that they may be shorted. In conjunction with the apparatus described below, closure of these shorted contacts 101 serves as a consistent signal to the main unit to initiate setup functions.

Alternatively, the connectors 105 of the patient-connection kit 100 may contain limited circuitry with a small amount of non-volatile memory in addition to the patient electrodes 125,130. The male portion of the connector 105 is offset eccentrically so that there is obviously only one way to connect it with another device. The connector 105 also contains a notch (or other irregular feature) that allows it to latch with its connection counterpart.

Figure 2:
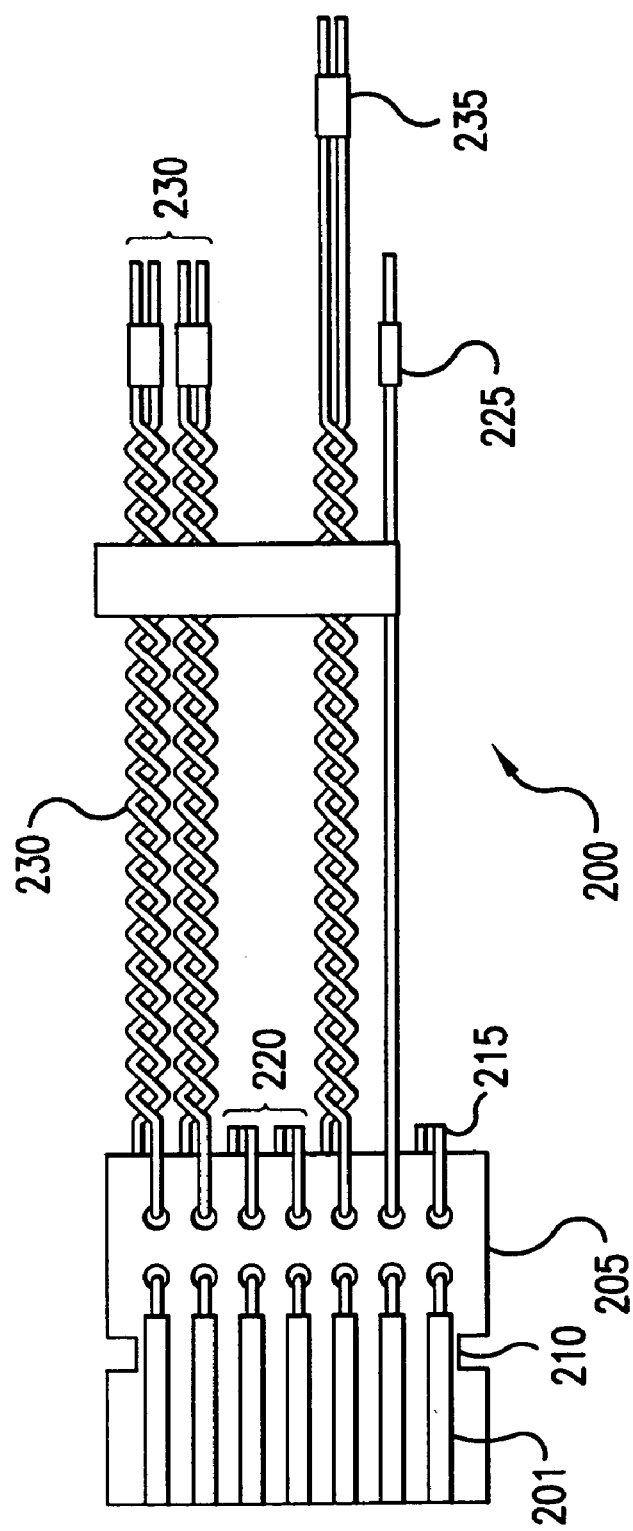
FIG. 2 is a diagram of another exemplary multi-electrode patient connection apparatus.

FIG. 2 is a exemplary diagram of another embodiment of a multi-electrode patient-connection apparatus or kit 200 with only two paired bipolar "intelligent" data electrodes 230 and one artifact-detection electrode 235 ("2+1"). As in FIG. 1, all electrodes 230,235 terminate in conductor strips or contacts 201 on a connector 205. Two other conductor pairs are so connected by a jumper 220 that signals to the main nerve integrity monitoring unit that those channels are not to be used for EMG recording. One unpaired connection is made with a single patient ground electrode 225.

In FIGS. 3A–3G, the patient connection recording harness 300 connects to the main chassis of the main monitoring unit by a male multi-pin connector 301. A transmission line cable 305 contains multiple pairs of wires, maximally treated for resisting electromagnetic artifact, a patient ground wire and multiple additional wire pairs. There is a re-enforced flexible plastic protective covering 310 in order to provide strain relief as the cable enters the main housing of the receiving portion of the harness 325.

A button 320 on the side of the housing of the receiving unit 325 releases connectors that are placed into the receiving unit. The housing of the receiving unit 325 accepts an adapter device 337, which permits the connection of individual patient electrodes that terminate in standard "protected" pin connectors. The adapter device 337 has a "male" connector portion 330, which is offset or constructed in such a manner so as to limit the connection to only a single orientation. The male connector portion 330 may also have a slot or other feature 335 to allow a spring-loaded retainer to hold the electrode firmly within the receiving housing 325.

On the terminal portion of the adapter device 337, the female connectors for accepting the "protected" pins of individual bipolar electrodes are closely spaced and (for minimizing the overall size of the adapter) arranged in pairs 340. There is also an unpaired single terminus for a patient ground electrode 345. As illustrated in this exemplary embodiment, the male portion 330 of the adapter 337 is made of double-sided PC board stock. The conductor strips or contacts 350 mate with contacts on the inside of the receiving housing. Looking onto the face of the receiving housing shows a slot 355 to accept the male connector portion 330 of the adapter 337.

Figure 4:
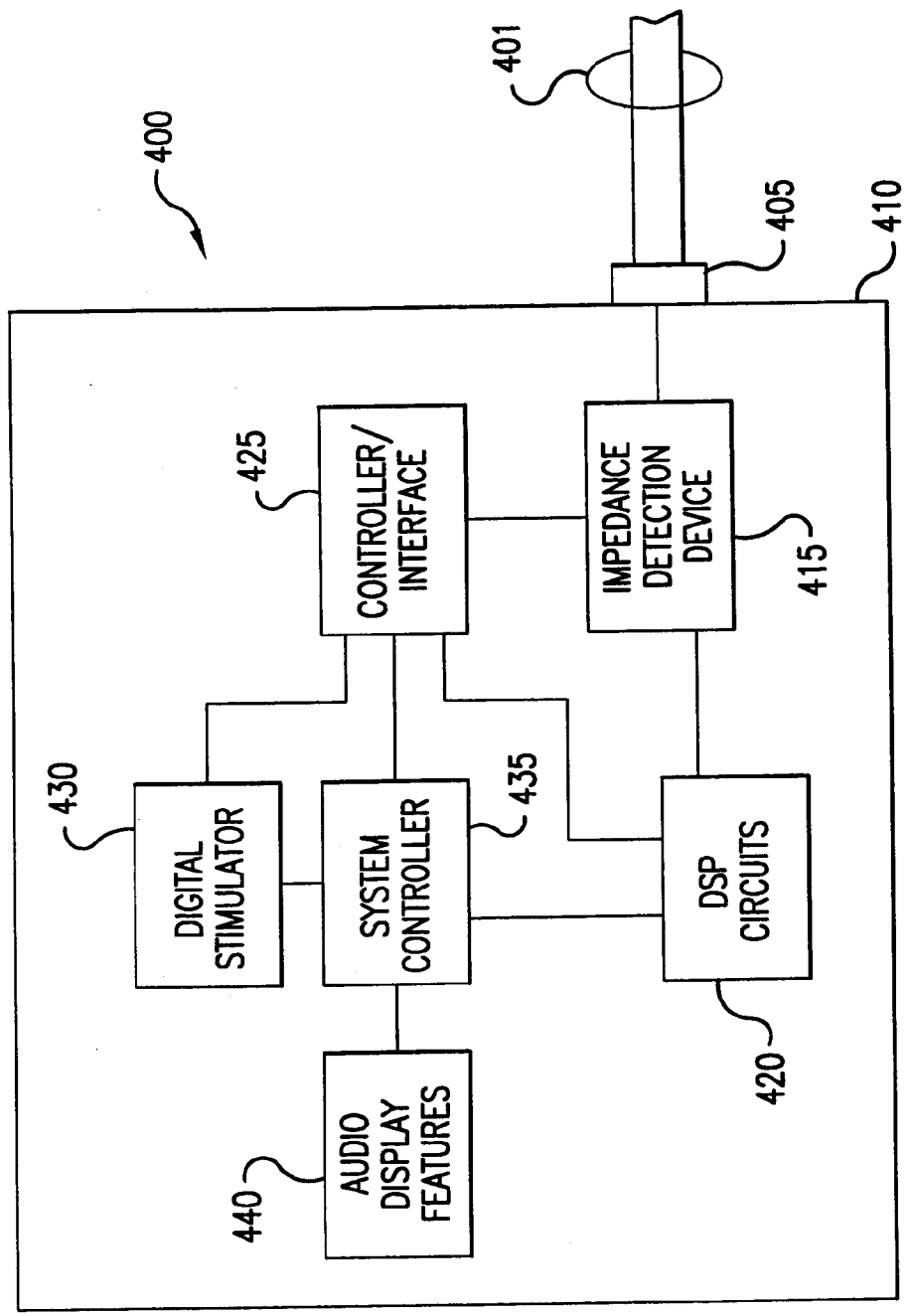
FIG. 4 is an exemplary block diagram of the automatic setup system.

FIG. 4 illustrates an exemplary cable transmission line portion 400 of the harness apparatus 401 that carries multiple data channels, maximally treated for resistance to electromagnetic field interference, a single patient ground electrode and at least three additional pairs of electrodes for communicating with the automatic setup apparatus. The "Harness" terminates in a male multi-connector 405 that mates with a female counterpart in the main chassis housing of the nerve integrity monitor 410. All wires are routed through an impedance detection device 415 that operates only during setup functions. EMG data is routed to recording amplifiers and DSP circuits 420. The electrode impedance measuring circuit 415 outputs to a controller/interface 425, which stores a programmable series of setup instructions, held in "non-volatile" memory. Based upon the pattern of impedances measured, the controller/interface 425 communicates setup instructions and parameters to a digital stimulator 430, a system controller 435 and the recording section 420 of the nerve integrity monitor. The system controller 435 can secondarily modify parameters, based upon other front panel (or other) input. Front panel indicators and audio display features 440 demonstrate results of diagnostics and important aspects of setup parameters.

The patient-connection harness pertains to a device that accepts the connector of the kits and contains a long transmission line (wires) and eventually terminates in a multi-pin connection at the main nerve integrity monitoring unit. The receiving portion of the harness is as small as possible, preferably less than two or three inches in any dimension, in order that it may easily fit on top of the operating table next to the patient.

The receiving portion of the harness has an eccentric offset that re-enforces a single orientation with the connector of the patient-connection kits. There is also a latch mechanism that fits into a notch located on the kit connector. A push-button mechanism allows release of the latch upon depression. Otherwise, the kit connector is held firmly within the receiving portion of the harness. The transmission line portion of the harness is 16 feet in length, for example. This is to allow the main monitoring unit to be situated approximately 10 feet from the operating table. The remaining 6 feet allow the receiving portion of the harness to extend from the floor to the top of the operating table. Within the transmission line of the harness the wires related to electrode data are maximally treated to give high resistance to electromagnetic interference. This is preferably accomplished with shielded, twisted pair wiring. However, other treatments, such as individually shielded coaxial wires, are available and effective. The wires related to the additional pairs of contacts on the connector of the "kits" are treated with simple insulation and without individual shielding. The harness finally terminates in a male multi-pin connector that mates with a female connector at the main chassis of the nerve integrity monitor.

Inside the main chassis of the nerve integrity monitor, all electrode lead and additional lead pairs will be routed to an impedance detection circuit. Except for brief periods of activation, the impedance detection circuit allows a clean (low-noise) "pass-through" condition of the EMG electrode signals. When the patient-connection kit is connected to the harness, the impedance detection circuit measures zero impedance for the contact pair that is always shorted in the patient connection kits. This signal initiates automatic setup functions.

As part of the automatic setup function, the impedance detection circuit measures the impedance of each EMG electrode pair and for the additional contact pairs. Impedance information regarding EMG electrodes is displayed by front panel CRT or LCD screen. The results of impedance measurement for both the EMG electrode leads and the additional contact pairs is communicated to a software controller interface, which actuates automatic setup of stimulus, recording and quantitative assessment parameters through a system controller, by triggering one of multiple stored setup algorithms. Preferably, these algorithms are stored on non-volatile memory in order that the setup parameters will be resistant to line surges and accidental unplugging. The system controller may indicate "pass" or "fail" of various internal diagnostic checks by front panel lighted indicators, audio tones, sound samples or voice samples.

The present embodiment is adapted to a monitoring device with four EMG data channels and an artifact-detection electrode. By the described method, the status of each of the additional contact pairs on the connector of the patient-connection kits, among open, closed (shorted) or specific fixed resistance conditions, may be configured to inform the main unit of a particular intent on the part of the surgeon. For example, it might indicate that the surgeon has chosen a patient connection kit, which is used for monitoring parotidectomy procedures, which involve a four channel setup and all four channels are displayed to the surgeon via loudspeaker.

Alternatively, in another embodiment of the kit, one of the paired bipolar electrodes might be sacrificed in favor of a pair of surface electrodes to be used monopolar (summating) arrangement for quantitative measurements. The status of impedance among the additional contact pairs might inform the main unit that the channel involving surface electrodes should not be included in audio feedback to the surgeon and that all quantitative determinations are to be routed to the "quantitative" channel. Still another embodiment might involve a kit containing two EMG electrodes. The connector is the same as for four channel versions. The locations on the connector where two electrodes are omitted are shorted by a jumper, which provides additional signals to the main unit regarding a two-channel setup.

A preferred approach for automatic setup is for an initial "signature" sequence followed by a "diagnostic" sequence. The "signature" sequence refers to a routine that involves lighting of channel and threshold indication LED's and corresponding audio representations (if different tones are sound designations are used for different channels) in an ordered and recognizable sequence. During this sequence all channel indicators light (or blink) and audio indicators sound in sequence, regardless of any problems or how many electrodes are being used. This gives the user a "memory" or impression of full unit function.

During a second time through, termed here as a "diagnostic" sequence, the process is repeated. However, the unit stops in the sequence, when it perceives a problem, such as with impedance mismatches or electrode disconnection. The second sequence represents a diagnostic "review" of important parameters. If a problem is perceived in one of the data channels, the sequence stops and an indicator light might blink in relation to the problem channel and an error message might appear in a CRT/LED display. Consistent sequences that route through the functions of the unit will likely make the user more aware of proper and improper functioning of the unit.

The exemplary stimulating and recording electrode connection embodiment shown in FIG. 5 will now be discussed.

Intraoperative nerve integrity monitoring involves the recording of electromyographic signals from muscles supplied by nerves to be monitored during surgical procedures. In addition, a stimulus probe is used to apply small electrical currents in order to locate and map the contour of the nerve to be monitored, as well as, to assess nerve function. Nerve integrity monitoring devices include both recording and stimulating functions.

In order to accomplish connection of the patient electrodes to its main portion, monitoring devices provide either a single cable with a single (common) "head box" for attachment of both stimulus and recording electrodes. Alternatively, two separate cables and separate head boxes to separately accommodate recording and stimulus electrodes. The most commonly used devices employ the single head box configuration.

Recording electrodes are typically placed and connected to the monitoring device after general anesthesia, but before sterile draping of the surgical field. Electrical stimulus probes are usually "passed off" in a sterile fashion and connected to the monitoring device after draping has been completed. If both recording and stimulation are to be employed, a head box with both recording and electrical stimulating electrode connections in a single housing must be placed where it can be accessed after sterile surgical draping. This location is usually somewhere underneath the plane of the operating table and away from knees and feet of operating surgeons and may be a few feet from the site of recording electrode placement.

Recording electrodes are typically designed with adequate lead length to span this distance. However, the longer length renders the electrodes more susceptible to electromagnetic and mechanical artifacts. Devices with separate head boxes for stimulating and recording electrodes allow placement of the recording portion closer to the site of electrode placement without affecting the accessibility of the stimulation portion. However, the separate arrangement is less popular, possibly due to cost or to perceived complexity of setup with two separate cables and connection housings.

Figure 5:
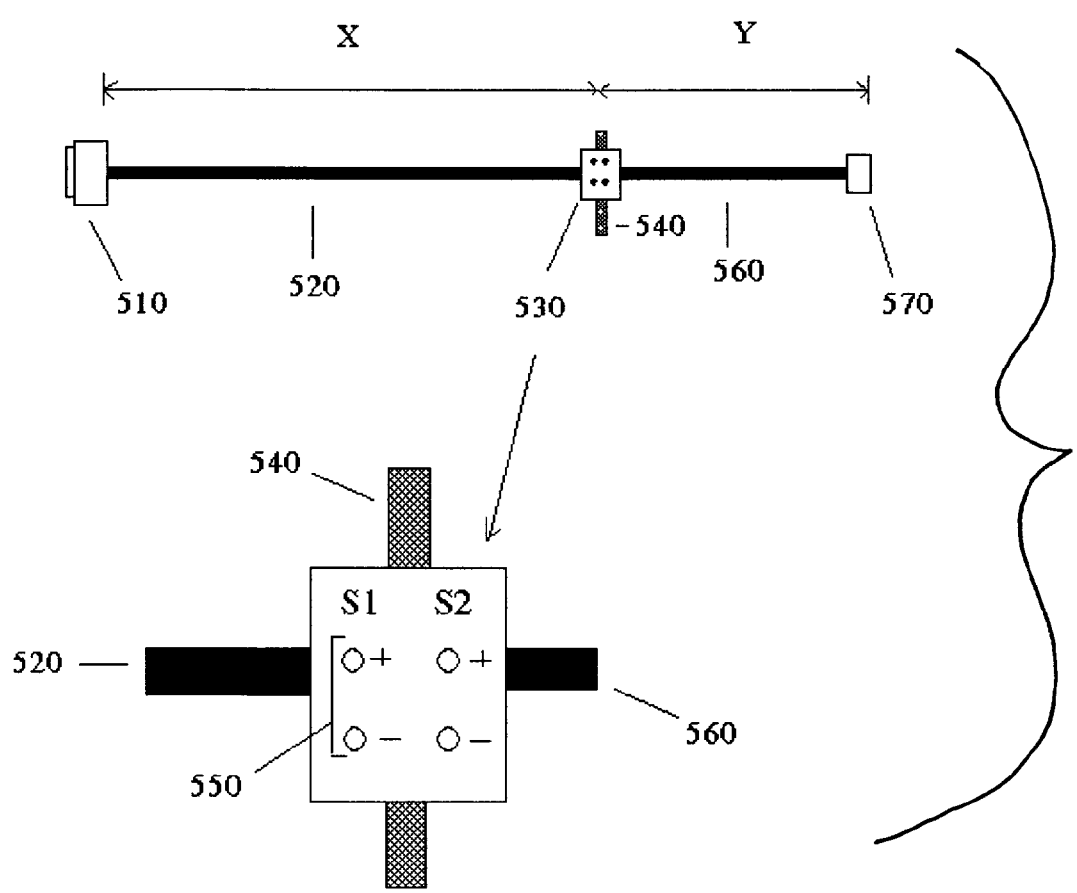
FIG. 5 is an exemplary diagram of a connection system for stimulating and recording electrodes.

The embodiment shown in FIG. 5 involves the incorporation of both stimulation and recording electrodes with a single cable, but with the head boxes for recording and stimulation arranged in a staggered fashion along that cable. The recording electrode portion appears at the terminal end of the cable and can be placed at the site of recording electrode placement. This arrangement allows use of shorter length electrodes, which may be cheaper to construct and less susceptible to electromagnetic and mechanical (drape movement) artifacts. The stimulus portion is positioned more proximate to the main unit by several feet (for example, 6 feet). After the recording portion is properly positioned, the stimulus connection box will be approximately at its optimal positioning for access after surgical draping. The all-in-one construction would obviate the need to separately place a stimulus head box apparatus, as for devices that include separate recording and stimulation head boxes and associated cabling.

In particular, the FIG. 5 embodiment involves a modification of the device illustrated in FIGS. 3A–3G. While the apparatus shown in FIGS. 3A–3G includes connections for only recording electrodes, the FIG. 5 embodiment includes both stimulating and recording electrode connections. The main unit connector 510 includes connections to the electrical stimulus source(s) in addition to connections for recording and automatic setup. Similarly, from the main connector, the main cable 520 contains wires to carry stimulus current, as well as, wires for recording and automatic setup.

The stimulator "head box" 530 may be permanently fixed or detachably attached to the main cable and has attached straps 540 (e.g., Velcro) in order to support the box in an appropriate fashion to the undercarriage of the operating table. The head box 530 (or connection unit) provides standard "protected" connection termini 550 to accommodate one or more pairs of stimulus probe (cathode) and anode electrodes. For example, the exemplary embodiment in FIG. 5 shows two separate pairs of stimulator connections S1 and S2.

A portion of the cable 560 continues beyond the bead box 530 toward its terminus connector 570. This portion of the cable 560 carries only the wires associated with recording and automatic setup. The cable 560 terminates in a connector 570, that accepts patient-connection kits as described above, or an adapter, which accepts standard protected pin connectors.

While this invention has been described in conjunction with specific embodiments thereof, it is evident that many alternatives, modifications, and variations will be apparent to those skilled in the art. Accordingly, preferred embodiments of the invention as set forth herein are intended to be illustrative, not limiting. Various changes may be made without departing from the spirit and scope of the invention.

For example, the connector type described above is exemplary and therefore not critical to the above embodiments. In addition, the possible conditions of the extra pairs of electrode leads carrying information regarding setup instructions, need not be limited to any particular circuitry. For example, a straight jumper connection may be replaced by fixed resistors of varying value. The values may be chosen so that they are sufficiently different from one another to allow a probe circuit from the main unit to easily differentiate which resistance values are present. The pattern of open circuit and resistance among the extra electrode pairs will give a much greater variety of potential information that might be transferred to the main unit. Furthermore, the stimulus electrodes may be also be connected to the cable 560 in any fashion either fixed or attachable.

What is claimed is:

1. A connection system for a nerve integrity monitoring system, the nerve integrity monitoring system having means for receiving and/or transmitting recording, set-up and stimulus signals, the connection system comprising:

one or more first transmission lines having a first connector at a first end and a second connector at a second end, at least one said connector adapted to be connected to the receiving and/or transmitting means, the one or more first transmission lines carrying at least said recording, set-up and stimulus signals to and from the receiving and/or transmitting means;

and a connection unit attached to the one or more first transmission lines between the first and second connectors, wherein one or more second transmission lines carrying the stimulus signals are connected to the connection unit.

2. The apparatus of claim 1, wherein the first connector is adapted to be coupled to the nerve integrity monitoring system, and allows transmission of recording, set-up and stimulus signals to and from the nerve integrity monitoring sdystem.

3. The apparatus of claim 1, further comprising at least one of recording electrodes, set-up electrodes, combined recording/set-up electrodes, a recording harness, a set-up harness, a recording and set-up harness, and an adapter that is adapted to be attached to a patient, wherein the second connector is coupled to at least one of said recording electrodes, set-up electrodes, combined recording/set-up electrodes, a recording harness, a set-up harness, a recording and set-up harness, and an adapter that is adapted to be attached to a patient, the second connector allowing transmission of recording and set-up signals.

4. The apparatus of claim 3, wherein the connection unit operates to divide the one or more first transmission lines into a first segment and a second segment, the first segment having the first connector and allowing transmission of recording, set-up and stimulus signals, and the second segment having the second connector and allowing transmission of recording and set-up signals to and from at least one of the recording electrodes, set-up electrodes, combined recording/set-up electrodes, a recording harness, a set-up harness, a recording and set-up harness, and an adapter that is adapted to be attached to a patient.

5. The apparatus of claim 1, further comprising stimulus probe and anode electrodes and wherein the one or more second transmission lines are attached to the stimulus probe and anode electrodes.

6. The apparatus of claim 1, wherein the connection unit includes an attachment device that permanently fixes the connection unit to the one or more first transmission lines.

7. The apparatus of claim 1, wherein the connection unit includes an attachment device that allows the connection unit to be detachably attached to the one or more first transmission lines.

8. The apparatus of claim 1, wherein the connection unit includes an attachment device that allows the connection unit to be detachably attached to an operating table.

9. A nerve integrity monitoring system, comprising:
the apparatus of claim 1.

10. A nerve integrity monitoring system comprising:
means for receiving and/or transmitting recording, set-up and stimulus signals;
one or more first transmission lines having a first connector at a first end and a second connector at a second end;
one or more second transmission lines having one or more connectors;
a connection unit positioned between the first and second connectors comprising:
a first attachment means for attaching the one or more first transmission lines to the receiving and/or transmitting means; the first connector for connection to the receiving and/or transmitting means and allowing transmission of recording, set-up and stimulus signals to and from the receiving and/or transmitting means; and
a second attachment means for receiving said one or more connectors from the one or more second transmission lines,
wherein the one or more first transmission lines carry at least said recording, set-up and stimulus signals to and from the receiving and/or transmitting means and the one or more second transmission lines carry said stimulus signals.

11. The nerve integrity monitoring system of claim 10, wherein the first attachment device permanently fixes the connection unit to the one or more first transmission lines.

12. The nerve integrity monitoring system of claim 10, wherein the first attachment device allows the connection unit to be detachably attached to the one or more first transmission lines.

13. The nerve integrity monitoring system of claim 10 further comprising stimulus probe and anode electrodes adapted to be received by the second attachment means, wherein the one or more second transmission lines are attached to the stimulus probe and anode electrodes.

14. The nerve integrity monitoring system of claim 10, wherein the first attachment means allows the connection unit to be detachably attached to an operating table.

15. The nerve integrity monitoring system of claim 10, wherein the second attachment means includes at least one of male connectors and female connectors.

16. A method for operating a nerve integrity monitoring system, comprising:
transmitting at least recording, set-up and stimulus signals to and from the nerve integrity monitoring system using one or more first transmission lines having a first connector at a first end and a second connector at a second end; and
transmitting stimulus signals using one or more second transmission lines connected to a connection unit, the connection unit being attached to the one or more first transmission lines between the first and the second connectors.

\* \* \* \* \*